US008206972B2

(12) United States Patent
Hua

(10) Patent No.: US 8,206,972 B2
(45) Date of Patent: Jun. 26, 2012

(54) **GROWTH MEDIA AND SAPROPHYTIC USE FOR *PICHIA ANOMALA***

(75) Inventor: Sui-Sheng T Hua, Orinda, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 316 days.

(21) Appl. No.: 12/507,057

(22) Filed: Jul. 21, 2009

(65) Prior Publication Data
US 2010/0254957 A1 Oct. 7, 2010

Related U.S. Application Data

(63) Continuation-in-part of application No. 11/607,713, filed on Dec. 1, 2006, now Pat. No. 7,579,183.

(51) Int. Cl.
*C12N 1/16* (2006.01)
*C12N 1/00* (2006.01)
(52) U.S. Cl. .................... 435/255.1; 435/255.5; 435/938
(58) Field of Classification Search .................. None
See application file for complete search history.

(56) References Cited

U.S. PATENT DOCUMENTS 6,500,425 B1 * 12/2002 McLaughlin et al. ..... 424/93.51
7,579,183 B1 * 8/2009 Hua ........................... 435/255.2

OTHER PUBLICATIONS

Al Mazraawi, M.S., J.L. Shipp, A.B. Broadbent, and P.G. Kevan, "Dissemination of Beaweria bassiana by Honey Bees (Hymenoptera: Apidae) for Control of Tarnished Plant Bug (Hemmiptera: Miridae) on Canola" (2006) Environ. Entomol. 35(6): 1569-1577.
Whitlow, L. "Distillers grains carry higher mycotoxin risk" (2008) Feed Management 59(4): 29.

* cited by examiner

*Primary Examiner* — Vera Afremova
(74) *Attorney, Agent, or Firm* — Howard V. Owens; John D. Fado; Leslie Shaw

(57) ABSTRACT

A biologically pure culture of a yeast of the species *Pichia anomala* (WRL-076). The yeast is identified as NRRL Y-30842 and is applied to a site containing a deleterious microorganism. Further disclosed is a growth medium for increasing the viablility of yeast organisms.

4 Claims, 20 Drawing Sheets

(7 of 20 Drawing Sheet(s) Filed in Color)

US 8,206,972 B2

GROWTH MEDIA AND SAPROPHYTIC USE FOR *PICHIA ANOMALA*

CROSS REFERENCES TO RELATED APPLICATIONS

This application is a continuation-in-part of U.S. patent application Ser. No. 11/607,713, filed Dec. 1, 2006, which is hereby incorporated by reference in its entirety, including any associated sequence listings.

SUMMARY OF THE INVENTION

According to an embodiment of the invention is a biocontrol agent comprising *Pichia anomala* WRL-076. Preferably the biocontrol agent comprises *Pichia anomala* WRL-076 deposit number NRRL Y-30842.

A further embodiment of the invention is a biologically pure culture of a yeast of the species *Pichia anomala* WRL-076 deposit number NRRL Y-30842, or composition thereof, the culture capable of competitively inhibiting growth of a deleterious micro-organism on an agricultural crop to which a biologically effective amount of the culture is applied. *Pichia anomala*, is referred to herein as strain WRL-076.

A further embodiment of the invention is a composition comprising the biocontrol agent WRL-076 and a carrier. Any carrier that permits the biocontrol agent to be delivered to a target plant in a manner such that the biocontrol agent remains viable and pathogenic may be employed in the composition.

A further embodiment is a method of using *Pichia anomala* to inhibit aflatoxin producing microorganisms on pre harvest, post harvest and stored affected agricultural crops.

According to still further features in the described embodiments, the portion of a plant is selected from the group consisting of a stone fruit, a pome fruit, a citrus fruit, grapes, a vegetable, a flower bulb, an herb, a grain, a root, a leaf, a grain and berries.

According to further embodiments the yeast is supplied in an active or dormant physiologic state.

According to still further features in the described preferred embodiments the yeast is supplied in a physical form selected from a liquid suspension, an emulsion, a powder, granules, a lyophylsate and a gel. Additionally, a growth media for optimum yeast growth is disclosed containing trehalose, glucose and sorbitol.

According to still further features in the described embodiments the chemical antibiotic is a fungicide or an antimicrobial agent or a pesticide.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

DETAILED DESCRIPTION OF THE INVENTION

Figure 1:
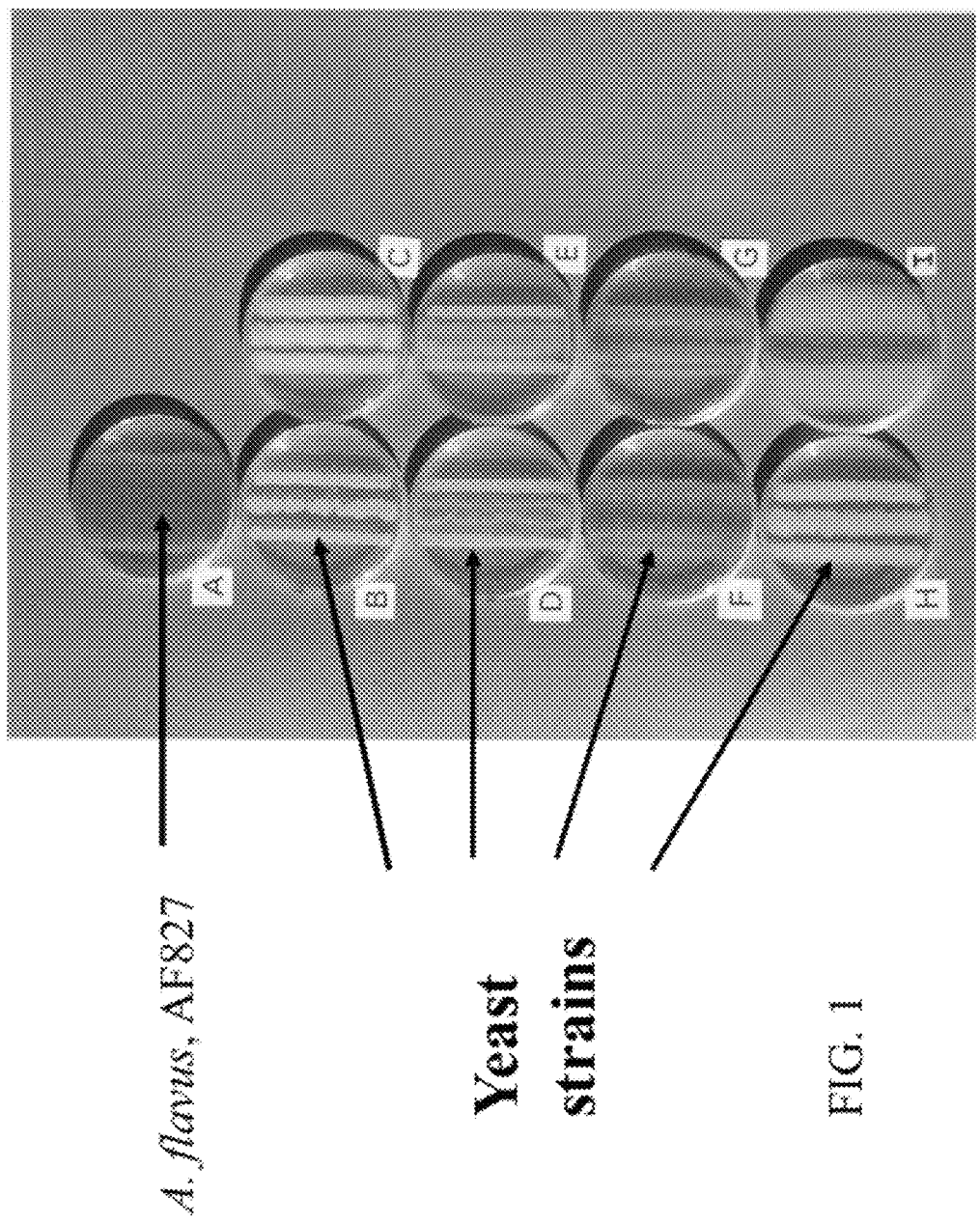
FIG. 1. is a photo of the efficacy of yeast species antagonistic to *Aspergillus flavus*. A nor mutant of *A. flavus* Papa 827 is used as an indicator strain for visual monitoring. (A) nor mutant in the absence of yeast; (B) to (G), different species of yeasts are applied to the agar plates as follows: WRL-076, WRL-038, WRL-084, WRL-015, WRL-024 and WRL-053.

The present invention is of a new yeast species *Pichia anomala* which can be applied to agricultural produce to reduce pre-harvest and postharvest decay via competitive inhibition of a wide range of micro-organisms.

Statement of Deposit

A biologically pure culture of *Pichia anomala* was deposited May 9, 2005 under terms of the Budapest Treaty with the Agricultural Research Service Culture Collection (NRRL) National Center for Agricultural Utilization Research, Agricultural Research Service, U.S. Department of Agriculture, 1815 North University Street, Peoria, Ill. 61604 USA and given the accession number NRRL Y-30842. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any isolate having the identifying characteristics of strains NRRL Y-30842, including subcultures and variants thereof which have the identifying characteristics and activity as described herein are included.

Specifically, the present invention can be used to reduce the incidence and/or severity of bacterial and fungal pathogens of nuts, grapes, citrus fruit, pome fruit, stone fruit, strawberries, flower bulbs, vegetables, roots, grains, foliage, and herbs.

"Grapes", as used in this specification and the accompanying claims, includes table grapes and wine grapes.

"Citrus fruit", as used in this specification and the accompanying claims, includes, but is not limited to, oranges, grapefruit, tangerines, clementines, lemons, limes, kumqwat, citroen, pomello, mandarin and hydrids derived therefrom.

"Pome fruit", as used in this specification and the accompanying claims, includes, but is not limited to, apples, pears and quinces.

"Stone fruit", as used in this specification and the accompanying claims, includes, but is not limited to, peaches, plums, nectarines, apricots, mangos.

"Nuts" as used in this specification and the accompanying claims, includes, but is not limited to tree nuts, such as, almonds, Brazil nuts, cashews, hazelnuts, macadamias, pecans, pine nuts, pistachios and walnuts; as well as peanuts.

"Grains" as used in this specification includes but is not limited to cereal grains, maize, rice, wheat, barley, sorghum, millets, oats, rye, triticale, buckwheat, fornio and quinoa.

For purposes of this specification and the accompanying claims the terms "inhibiting" and "inhibition" refer to retardation or delay of a process. As such, inhibition may be deemed to occur if the process occurs at a reduced rate as a result of application of a claimed yeast, a composition containing such a yeast, or as a result of practice of a claimed method.

A further embodiment of the invention is of methods of use of the claimed yeast, compositions containing the claimed yeast and articles of manufacture including those compositions in stored agricultural crops, bee hives or locales and animal feed.

The principles and operation of protection of agricultural produce against unwanted decay via competitive inhibition according to the present invention may be better understood with reference to the figures and accompanying descriptions.

According to another embodiment of the invention there is provided a biologically pure culture of a yeast of the species *Pichia anomala* identified as NRRL Y-30842. This culture is capable of competitively inhibiting growth of a wide range of deleterious micro-organisms on a portion of a plant to which a biologically effective amount of the culture is applied. A further embodiment is the use of the invention to combat a deleterious micro-organism on an agricultural crop or portion thereof, the method includes applying at least one time an agriculturally effective amount of a biologically pure culture of a yeast of the genus.

Any biologically pure strain of *Pichia anomala*, whether physically derived from the original deposit or independently isolated, is part of the present invention so long as it possesses all of the identifying characteristics of NRRL Y-30842. This includes biologically pure mutants of *Pichia anomala*, so long as they retain all of the identifying characteristics of NRRL Y-30842. For purposes of this specification and the accompanying claims, the term "mutant" includes both naturally occurring mutations and purposeful genetic modifications such as introduction of point mutations, plasmids, phages, phagemids, cosmids and artificial chromosomes.

The deleterious micro-organism which WRL-076 protects against include, but are not limited to, plant fungal pathogens found in, *Aspergillus* spp, including *flavus* and *parasiticus*, *Penicillium digitatum*, *Penicillium italicum*, *Penicillium expansum*, *Geotrichum candidum*, *Rhizopus stolonifer*, *Alternaria* spp., *Molinilia* spp, and *Fusarium* spp; *Botrytis* spp. as well as plant bacterial pathogens found in *Erwinia* spp., *Burkholderia cepacia* complex—(*B. cepacia* genomovar-I, III & VI; *B. vietnamiensis*, *B. multivorans*, *B. pyrrocinia*, *B. stabilis*, *B. ambifaria*), *Pseudomonas* spp., *Erwinia* spp., *Ralstonia* spp., *Rhizobium* spp., *Agrobacterium* spp.

The yeast of the composition may be supplied in any physiologic state such as active or dormant. Dormant yeast may be supplied, for example, frozen (e.g in DMSO/glycerol), dried or lyophilized. Further, the yeast of the composition may be supplied in any physical form including, but not limited to a liquid suspension, an emulsion, a powder, granules, a lyophylisate or a gel.

The composition may be applied as spray or drench or as an aerosolized powder or ointment. If the composition includes dormant yeast, they may require re-activation prior to use, for example by rehydration and or incubation in a nutrient medium. Preferably, dormant yeast will become active when applied or subsequent to application.

Production and Formulation of Biocontrol Yeast, *Pichia anomala* WRL-076

Both complex media such as NYDB (nutrient broth, 10 g, yeast extract, 8 g, dextrose 10 g per liter of water), PDB (potato dextrose broth) and ME (malt extract) and chemically defined media supplemented with a variety of carbon source such as glucose, sucrose, sorbitol, molasses etc. can be used to produce *P. anomala* by fermentation. Yeast cells will be harvested by centrifugation. The resulting yeast paste (wet biomass) will be preserved by adding salt, glycerol, lactose, trehalose, sucrose, amino acids to prolonged shelve-life during storage.

Trehalose and sorbitol traditionally used as compounds for storing yeast have been advantageously used with glucose as a growth medium for the claimed yeast as well as other Genuses of yeast. Trehalose is a disaccharide known for its role to protect cell integrity and function under adverse environmental conditions, such as drought and freezing. Arabitol is found in yeast cells under salt stress. We examined sugar and polyol profiles of yeast cells grown in four different media (see example 2). Medium D contains glucose, sorbitol and trehalose. When *Pichia anomala* grows in this medium, the accumulation of intracellular trehalose and sorbitol was observed. Interestingly, these two compounds were also exported outside the yeast cells and found in the supernatant.

We have tested over fifty varieties of medium composition to grow *P. anomala* WRL-076 in order to define the optimal media which could support high yield of cells. The definition of high yield of cells is to measured colony forming unit (CFU) on nutrient agar plates. A variety of sugars and polyols was tested as carbon sources, such as glucose, sucrose, molasses, glycerol, sorbitol, mannitol, maltose, trehalose. Regarding to nitrogen sources, such as ammonia, nitrate, urea, yeast extract, nutrient broth were tested. Four media were selected for the yield of cells summarized in Table 1. Nutrient broth and yeast extract are good nitrogen sources. For carbon sources, glucose, sorbitol and trehalose are used.

TABLE 1

Media Composition

| Mediium | Carbon Source | Nitrogen Source |
|---|---|---|
| A | 3% glucose | 0.8% Nutrient Broth and 0.5% Yeast Extract |
| B | 3% glucose and 3% Sorbitol | 0.8% Nutrient Broth and 0.5% Yeast Extract |
| C | 3% glucose and 1% Trehalose | 0.8% Nutrient Broth and 0.5% Yeast Extract |

TABLE 1-continued

Media Composition

| Mediium | Carbon Source | Nitrogen Source |
|---|---|---|
| D | 3% glucose and 3% Sorbitol and 1% Trehalose | 0.8% Nutrient Broth and 0.5% Yeast Extract |

The concentration of Glucose, sorbitol or trehalose within the media composition range from 1-5% (w/v).

Most commercial yeast products are produced by high speed centrifugation to separate the yeast cells from the liquid medium. The collected yeast cells were dried by freeze-drying, fluid bed drying. The dried products will be re-hydrated in water for use. These steps will definitely damage the cell walls and cause cell mortality. In this invention, the yeast cells were kept in a cylindric containers and stored in the cold room at 4° C. The yeast cells settled at the bottom in two days. One can remove the medium supernatant by siphoning out the liquid leaving a small amount of supernatant to cover the yeast cells. The viability of the yeast cells were monitored monthly by assessing the CFUs. After six months of storage, the viability of *P. anomala* cells did not decrease when the yeast cells grown in medium D. This approach requires minimal energy input.

The growth medium described herein may be used to support the growth of other yeast organisms used in food production by increasing the viability of the starter cultures during manufacturing. Among these are *Saccharomyces cerevisiae, Saccharomyces pastorianus, Saccharomyces boulardii. Sporobolomyces* spp., *Sporidiobolus* spp., *Rhodotorula* spp, and *Rhodosporidium* spp. are pigmented due the biosynthesis of β-carotene, torulene and torularhodin. These yeast species are widely used as natural pigments in food products and salmon fish. In addition food yeast *Candida utilis* (LycoYeast) produces primarily cis-lycopene, the bioactive form, while tomato extracts contain predominantly the less bioactive isomer trans-lycopene. Products can be developed and used as dietary supplements contain lycopene and other carotenoids, as well as high levels of protein and B-vitamins. Viable yeast cells in combination with beneficial bacteris such as *Lactobacillus, Bifidobacterium, Streptococcus, Lactococcus* are ingredients of probiotic products for supplements in human, animal and poultry diets.

Application of the yeast in liquid or suspension form to pre harvest, post harvest and stored sites in need may be accomplished by ground or aerial spraying using equipment routine to one of skill in the art. The nozzle of the sprayer may be adjusted for size by one of skill in the art to accommodate the size of the crop as well as the use of presently disclosed adjuvants and carriers.

A dry formulation of yeast, *P. anomala* WRL-076, can be produced by several drying methods including freeze drying, air drying, spray drying, or fluidized bed drying. Skim milk, sucrose, lactose etc., will be added to the yeast cells as protectants during the drying process. Corn meal, wheat flour, cotton meal, clay etc., will be used as carriers. The viability of formulated yeast cells will be monitored monthly up to one year.

Adjuvants may be used to increase the biocontrol activity of *P. anomala* during field application. These include surfactants such as Tween 80, BREAK THRU™; adhesion promoters such as sodium alginate, carboxymethylcellulose and chitosan; UV protectant such as solubilized lignin solution.

Potential Use of *Pichia anomala* in Post-Harvest Situations.

The biocontrol yeast, *P. anomala* WRL-076 can be incorporated in wax, shellac, food grade additives to be applied to harvested fruits to protect fruits from rot during storage. The biocontrol yeast can also be used in stored grains such as wheat, corn and barley to prevent mycotoxin contamination during storage.

The yeast find particular use in combating mycotoxins in distillers grains from corn. Distillers grains is a by-product derived from the ethanol industry. Ethanol production utilizes the starch in corn kernels, leaving a protein and fiber rich residue. A significant problem is the enrichment of mycotoxins. If the original corn is contaminated with mycotoxins, distillers grains produced from it can contain two to three times the amount of the original mycotoxin concentration, which is not acceptable as feedstuff. Mycotoxins are often synergistic, low levels of aflatoxin, fumonisin, zearalenone, ochratoxin etc. in the grains can become very toxic to human and animal. Aflatoxin is of great concern because it is a potent carcinogen and can be transferred to cow's milk if the animal fed with contaminated feedstuff.

In addition, *P. anomala* WRL-076 can also be used in combination with *Candida oleophilia, Metschnikowia pulcherrima* or *Aureobasidium pullulans* etc., for both pre-harvest or post-harvest control of fungal pathogens.

In order to increase the overall efficacy of the composition, a chemical antibiotic may be further included. The chemical antibiotic may be a compatible fungicide, for example Iprodione or Thiabendazole, Imazalil, Fenhexamide, Pyrimethamil or a combination of Fludioxonyl and Cyprodinil or a chemical equivalent thereof or a combination including same. Alternately, or additionally, the chemical antibiotic includes an antimicrobial agent or a pesticide.

*P. anomala* can be grown on any suitable solid or in liquid media. Solid media that can be used include nutrient-yeast extract-dextrose agar, V-8 agar, and malt extract agar. The strain may be grown in liquid media in any conventional shake flask at 28° C. on a shaker at about 150-200 rpm. For larger scale operations, it is convenient to grow the culture in a fermentation tank, while applying agitation and aeration to the inoculated liquid medium. The yeast cells are harvested by conventional sedimentary methodology, e.g., centrifugation or filtering. The cultures are stored at about 4° C. until use. Yeast stock culture was maintained on potato dextrose agar (PDA). Long term storage of yeast culture was carried out in 30% glycerol at −20° C.

*P. anomala* is useful to control pre-harvest and post-harvest fungal and bacterial pathogens in agricultural crops or commodities. For purposes of the invention, control means that the fungal growth and spore production is reduced or prevented. The commodities and crops include but are not limited to nuts, figs, wheat, cotton and corn. The strain can also be applied in fruits such as apples, pears, cherries, peaches, plums, berries, grapes and strawberries for both pre-harvest and post-harvest protection.

The yeast, *P. anomala* WRL-076 can be mixed with any agriculturally acceptable carrier. As used in this specification and the accompanying claims, the term "carrier" refers to any substance or diluent that does not cause significant irritation to agricultural produce or plants and does not abrogate the biological activity and properties of the administered active ingredient. As such, the term specifically includes, but is not limited to, inert solvents, aqueous solutions such as culture media, inert powders or solid carriers such as clay, alginate and diatomaceous earth.

Where the strain is applied as a suspension, the suspension may optionally contain conventional additives such as surfactants, wetting agents, and antioxidants. The yeast cells are applied in an effective amount. For the purposes of this invention, an effective amount is defined as that quantity of microorganism cells sufficient to inhibit the development of the targeted pathogens. Typically, a concentration range from about $1 \times 10^6$ to $1 \times 10^9$ colony forming units (CFU)/ml is effective. The preferred concentration range is from $1 \times 10^7$ to $1 \times 10^8$ CFU/ml. The yeast cells can be applied in water, physiological buffer, or in mixtures with lower rates of fungicides for control of pathogens.

The invention is further embodied by an article of manufacture which includes packaging material and a composition identified for use in protection of agricultural produce from a deleterious micro-organism. The article of manufacture includes, as an active ingredient, a biologically effective amount of yeast of biologically pure *Pichia anomala* and further contains a carrier. Preferably, the article of manufacture further includes an applicator designed and constructed to apply the yeast to the agricultural produce.

The claimed yeast species, compositions and articles of manufacture including same and methods of use thereof are expected to find great utility in commercial agriculture. Their utility stems from their broad spectrum of activity against important pathogens and from the wide range of plants/fruits to which they may be efficaciously applied. In addition, *P. anomala* may be applied in the field, or concurrent with harvest, or during storage. Further, as demonstrated in examples herein below, *P. anomola* is useful under a wide variety of storage conditions. Thus, an embodiment of the invention allows pre-harvest application of benign yeast as a means of preventing post-harvest decay of agricultural produce.

The claimed yeast may also be combined with bees wherein the bees serve as a delivery vector for *Pichia anomala*. Field application of either fungicide or biocontrol agents with a spray apparatus will not effectively cover all the infection sites of deleterious microorganisms. Bees are used by commercial fruit growers to improve flower pollination because they forage daily and can provide more precise delivery to flowering agricultural crops. Pollen dispensers are placed inside the beehive and exiting bees acquire pollen as they leave the hive and deliver the pollen to flowers. *Pichia anomala* and suitable compositions thereof may be sprayed or placed in an existing pollen dispenser or separate apparatus, capable of controlled release, which provides for dispensing the *Pichia anomala* to a hive or attractant locale for delivery of the yeast to agricultural crops, including flowering crops. The hives or locales of bees which engage in pollination are preferably targeted for use with the yeast of the invention, particularly honeybees, carpenter bees, digger bees, leafcutter and mason bees, sweat bees, cellophane bees, orchid bees and Africanized honeybees.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed below finds experimental support in the following examples.

Yeast Isolation and Identification

Two hundred strains of yeasts were isolated from the external surfaces of buds, twigs, leaves, fruits, nuts of pistachio and almond (tree and ground sources). Plant samples were transferred to a flask containing Tween-80 water (0.05% Tween 80), followed by vortexing and shaking, ultrasound has also been employed to facilitate the dislodgement of higher numbers of yeasts species. The microbial suspension was plated on nutrient agar media. Yeast colonies were purified by streaking each single colony on agar medium.

A visual bioassay was developed to screen for antagonistic activity against *Aspergillus flavus*, Papa 827 as well as other isolates of *A. flavus*. We used the following bioassay protocol: (i) the yeast isolate was grown in a flask containing potato dextrose broth (DIFCO™) for 24 h on a shaker at 28° C., and the fresh culture was used for inoculation; (ii) spore suspensions of the nor mutant were prepared ($10^4$ spores/ml); (iii) two streaks of 20-μl yeast cultures were applied 15 mm from the center line of a petri dish containing PDA; (iv) 4 h later, 20 μl of the *A. flavus* spore suspension was inoculated along the center line of the PDA agar; (v) the petri dish was sealed with Parafilm M (American National Can, Neenah, Wis.) and incubated at 28° C. for 10 days. We determined the effects of yeast isolates on *A. flavus* by visually estimating the amount of red-orange color formed by the nor mutant (FIG. 1). A score of ++++ was assigned to the bright orange pigment level of control (FIG. 1A), and a score of ---- was assigned to an almost imperceptible level of pigment (FIGS. 1B and C). The growth of the nor mutant was restricted to and reduced within the boundary of the two streaks of the yeast zone in the bioassay (FIG. 1). As shown in FIG. 1, the fungal colony expanded toward the edges of the PDA in the petri dish in the absence of the yeasts as shown in FIG. 1. The visual bioassay described here provides a simple and useful monitoring system for screening large numbers of yeast strains for their effectiveness in blocking early steps of the polyketide pathway in the biosynthesis of aflatoxin by *A. flavus*. The nor mutant also is safer for use in routine experiments than is a wild-type strain of *A. flavus*, since the mutant produces little if any aflatoxin during routine laboratory culture.

Two hundred strains of yeasts were screened for their potential to prevent the growth of *A. flavus* by a visual bioassay. A few species of yeasts have been identified to be effective in inhibiting both the growth of *A. flavus* and aflatoxin production (Hua, et al., 1998, Hua et al., 1999). One isolate, WRL-076 was effective in inhibiting both the growth and aflatoxin production of *A. flavus*. The yeast were identified to be *Pichia anomala* by Central Bureau for Fungal Culture (CBS), Baarn, the Netherlands, based on morphological characteristics, fermentation of sugars, and growth on different carbon and nitrogen sources.

The biocontrol efficacy of a strain of yeast, *P. anomala* WRL-076, was evaluated further on pistachio flowers, leaves, nut-fruits and almond leaves. Spore production of *A. flavus* was reduced by about 80% in pistachio flowers sprayed with the yeasts. It was also effective in decreasing spore production by 40-60% on almond and pistachio leaves sprayed with *P. anomala* WRL-076. Wounded pistachio nut fruits inoculated with yeast decrease spore production of *A. flavus*. Almond nuts sprayed with the yeast showed much less fungal growth.

Figure 2:
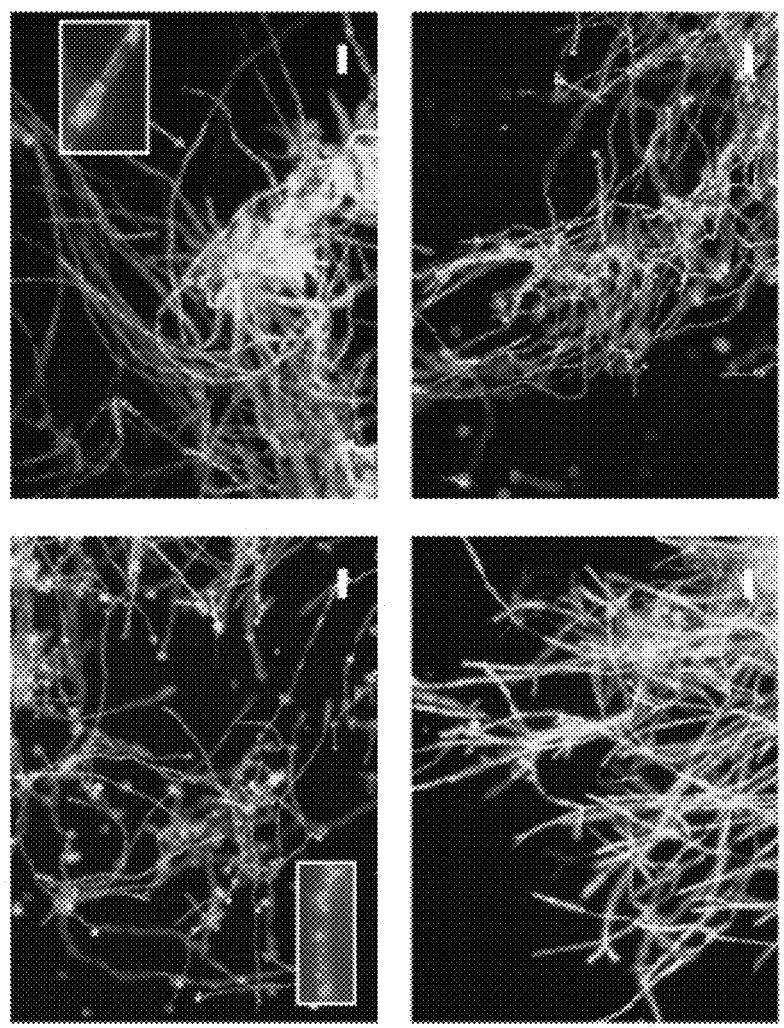
FIG. 2. is a photo of epifluorescence micrographs of live, yeast treated, and heat killed *Aspergillus flavus* stained with FUN-1 viability stain. Metabolically active *A. flavus* hyphae accumulated red fluorescence in vacuoles, while hyphae that were inhibited by *P. anomala* WRL-076 stained green.

FUN-1 [2-chloro-4-(2,3dihydro-3-methyl(benzo-1,3-thiozol-2-yl)-methylidene)-1-phenylquinolinium iodide] stain is a membrane-permeant, halogenated cyanine compound that binds nucleic acids and has an unique and useful property. FUN-1 stain was used to assess damage of hyphae by antifungal agents in several species of *Aspergilli* (Lass-Florl et al, 2001; Marr et al, 2001; Balajee et al., 2002). These studies show that FUN-1 is useful as a viability stain to monitor the metabolic status of yeast and fungi. FUN-I was used to visualize the metabolic status of *A. flavus* grown in the presence or absence of the biocontrol yeast in potato dextrose broth. Metabolically active *A. flavus* hyphae accumulated red fluorescence in vacuoles, while hyphae that were inhibited by *P. anomala* WRL-076 stained green. Red fluorescence accumulation in the vacuoles was greatly reduced in *A. flavus* hyphae when the yeast to fungus ratio was 50 (FIG. 2).

The yeast, WRL-76 was identified as *Pichia anomala* (E. C. Hansen) Kurtzman according to standard procedures. Characteristics are: fermentation is present; cells are pink colored, lemon-shaped; Pseudo hyphae are visible from colony margins.

Additional information regarding growth characteristics of isolates *Pichia anomala* WRL-076 is given below:

| WRL-076 | |
|---|---|
| D-glucose | + |
| D-galactose | v |
| L-sorbose | − |
| D-glucosamine | − |
| D-ribose | − |
| D-xylose | + |
| L-arabinose | − |
| L-rhamnose | − |
| sucrose | + |
| maltose | + |
| trehalose | + |
| methyl-glucoside | + |
| cellobiose | + |
| melibiose | − |
| lactose | − |
| raffinose | + |
| melezitose | + |
| glycerol | + |
| meso-erythritol | + |
| D-glucitol | + |
| D-mannitol | + |
| myo-inositol | − |
| 2-keto-D-gluconate | + |
| D-gluconate | v |
| D-glucuronate | − |
| DL-lactate | + |
| nitrate | + |
| ethylamine | + |
| lysine | + |
| cadaverine | + |
| growth at 25. degree. C. | + |
| growth at 30. degree. C. | + |
| growth at 37. degree. C. | poor |

DNA sequence analysis of large subunit ribosome using the universal primer pair, NL1 and NL2 shows that *P. anomala* WRL-076 has the following sequences:

CCACAGGGATTGCCTCAGTACGGCGACTGAAGCGGCAAAAGCTCAAATTT

GAAATCTAGCACCTTCGGTGTTCGAGTTGTAATTTGAAGATGGTAACCTT

GGGTTTGGCTCTTGTCTATGTTCCTTGGAACAGGACGTCATAGAGGGTGA

GAATCCCGTCTGATGAGATGCCCATTCCTATGTAAGGTGCTATCGAAGAG

TCGAGTTGTTTGGGAATGCAGCTCTAAGTGGGTGGTAAATTCCATCTAAA

GCTAAATATTGGCGAGAGACCGATAGCGAACAAGTACAGTGATGGAAAGA

TGAAAAGAACTTTGAAAAGAGAGTGAAAAAGTACGTGAAATTGTTGAAAG

GGAAGGGCATTAGATCAGACTTGGTGTTTTACGATTATCTTCTCTTCTTG

AGTTGTGCACTCGTATTTCACTGGGCCAGCATCGATTCGGATGGCAAGAT

AATGGCAGTTGAATGTGGCTTCACTTCGGTGGAGTGTTATAGCTTCTGCT

GATATTGCCTGTCTGGATCGAGGGCTGCGTCTTTTGACTAGGATGCTGGC

GTAATGATCTAATGCCGCCCGTCG

The result of Blast against GenBank data base indicate that *P. anomala* strain WRl-076 is a bona fide species of *Pichia anomala*.

Aflatoxin contamination is associated with wounding in corn, peanut, cotton seed and tree nut (Diener et al, 1987; Payne, 1992; Cotty et al, 1994; Hua et al, 1998). Assessment of the efficacy of *P. anomala* has been achieved by mechanically wounding pistachio nuts on the tree in the orchard to increase the number of wounded nuts. The results clearly demonstrate that the production of *A. flavus* spores was drastically inhibited by spraying yeast onto wounded pistachio nuts. One can anticipate that field spraying of this effective yeast to pistachio trees will decrease the population of *A. flavus* in the orchards. The outcome will be a reduction of aflatoxin contamination in the edible nuts. Using pistachio as a model system, similar results can be predicted for almond and corn.

The following examples are intended only to further illustrate the invention and are not intended to limit the scope of the invention which is defined by the claims.

EXAMPLES

Example 1

Growth Inhibition of nor Mutant

To measure growth inhibition of the nor mutant, we determined the dry weight of the fungal mass in the agar between the two streaks of yeast. Five agar discs (7-mm diameter) of fungal mycelium were cored and transferred to boiling water. The floating mycelial mat was washed once in boiling water to remove agar traces and air dried at room temperature for 16 h. The dry weight of the fungal mass depended upon the yeast strain in the petri dish. Growth and norsolorinic acid were not correlated (r=0.43 and p=0.18 based on the Kendall correlation), so the yeasts must affect norsolorinic acid accumulation in some manner other than simply reducing the amount of biomass available to accumulate the compound.

TABLE 2

Effects of saprophytic yeasts on *Aspergillus flavus* strain Papa AF 827

| Yeast | Norsolorinic acid (mg/5 discs) | Biomass (mg/5 discs) |
|---|---|---|
| WRL-015 | 16 ± 2.1 | 7.2 ± 0.7 |
| WRL-024 | 66 ± 8.3 | 6.8 ± 0.7 |
| WRL-038 | 3 ± 0.4 | 5.5 ± 0.5 |
| WRL-053 | 60 ± 7.2 | 7.0 ± 0.6 |
| WRL-076 | 4 ± 0.8 | 3.8 ± 0.4 |
| WRL-084 | 21 ± 3.5 | 4.5 ± 0.4 |
| Control | 112 ± 12 | 8.8 ± 0.7 |

Example 2

Inhibition of Aflatoxin Biosynthesis

Figure 3:
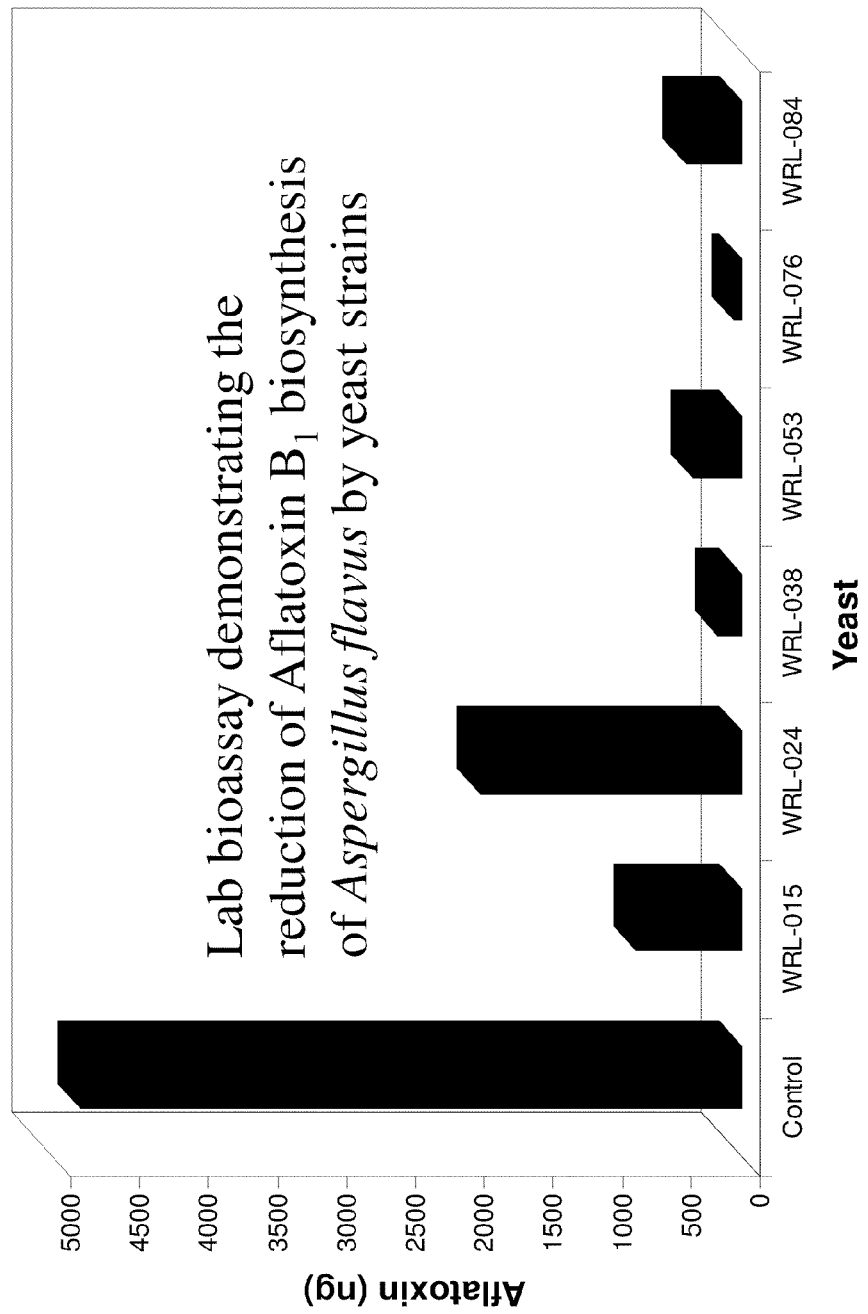
FIG. 3. is a graph of the effects of different yeast species on aflatoxin production by a toxigenic strain of *Aspergillus flavus* 42-12.

A toxigenic strain *A. flavus* 42-12 was used to test the effectiveness of the six yeasts for inhibiting aflatoxin biosynthesis in the bioassay. Four agar discs (7-mm diameter) of fungal cultures were cored in the center of a petri dish and transferred to a glass tube containing methanol. Aflatoxin was extracted and analyzed by high performance liquid chromatography. When grown on PDA, strain 42-12 produced 4,800 ng of aflatoxin per four discs. Aflatoxin production was drastically reduced by yeasts WRL-076 and WRL-038 and moderately reduced by WRL-015, WRL-053, and WRL-084 (FIG. 3).

Example 3

The Effect of the Yeast on the Growth of *A. flavus* was Evaluated on Pistachio Male Flowers The male flowers were collected from orchards and sterilized by autoclave. Five gram of male flowers were weighted and placed in a Petri dish. Spore suspension of *A. flavus* was prepared in Tween 80 solution (0.05%) and yeast suspension was prepared in sterile water. A Beckman-Coulter Multisizer was used to determine the number of spore and yeast. The yeast suspension was adjusted to $10^8$/ml and the spore suspension to $10^4$/ml. Samples (Y+F) were each sprayed with 2 ml of yeast suspension and incubated at 28° C. for 24 h, and then each sprayed with 2 ml of spore suspension. After the treatment, the samples were incubated at 28° C. Triplicate samples were analyzed for colony forming units (CFU) of yeast and fungal spore on day 1, day 7 and day 15.

One set of samples (Y) were each sprayed with 2 ml of yeast suspension and 2 ml of water, and then incubated at 28° C. for monitoring the growth of yeast. The number of yeast on the flowers were evaluated on day 1, day 7 and day 15. In addition, one set of samples (F) were sprayed with 2 ml of spore suspension and 2 ml of water, then incubated at 28° C. to monitor the growth of *A. flavus* in the absence of yeast and analyzed on day 1, day 7 and day 15.

Figure 4:
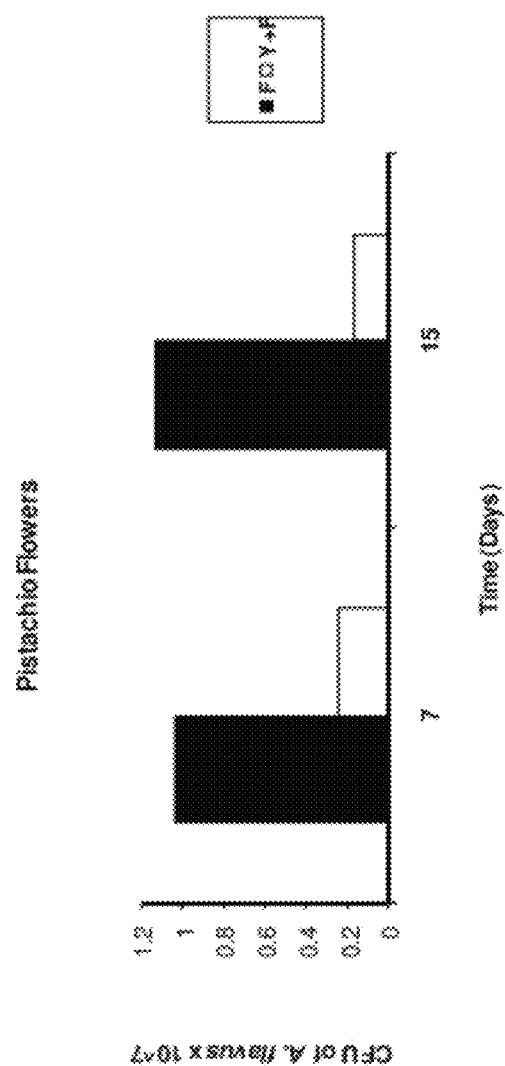
FIG. 4. is a graph of the inhibition of *Aspergillus flavus* spore production by the yeast, *Pichia anomala* WRL-076. Pistachio flowers were used as the experimental materials. Viable spores were determined by counting clony forming units (CFU) on nutrient agar.

Yeast and fungal spores were eluted in Tween 80 solution from the experimental samples by shaking and sonicating in flasks. A spiral plating system was used to spread the yeasts or spores onto nutrient agar. The CFU of yeast and *A. flavus* on the agar plates were counted using the spiral counting formula. FIG. 4 shows that spore production of *A. flavus* increased over a period of 15 days. In flowers sprayed with yeast, spore production was reduced by 80%.

Example 4

Field Evaluation of the Efficacy of the Biocontrol Agent, *P. anomala* WRL-076

Figure 5:
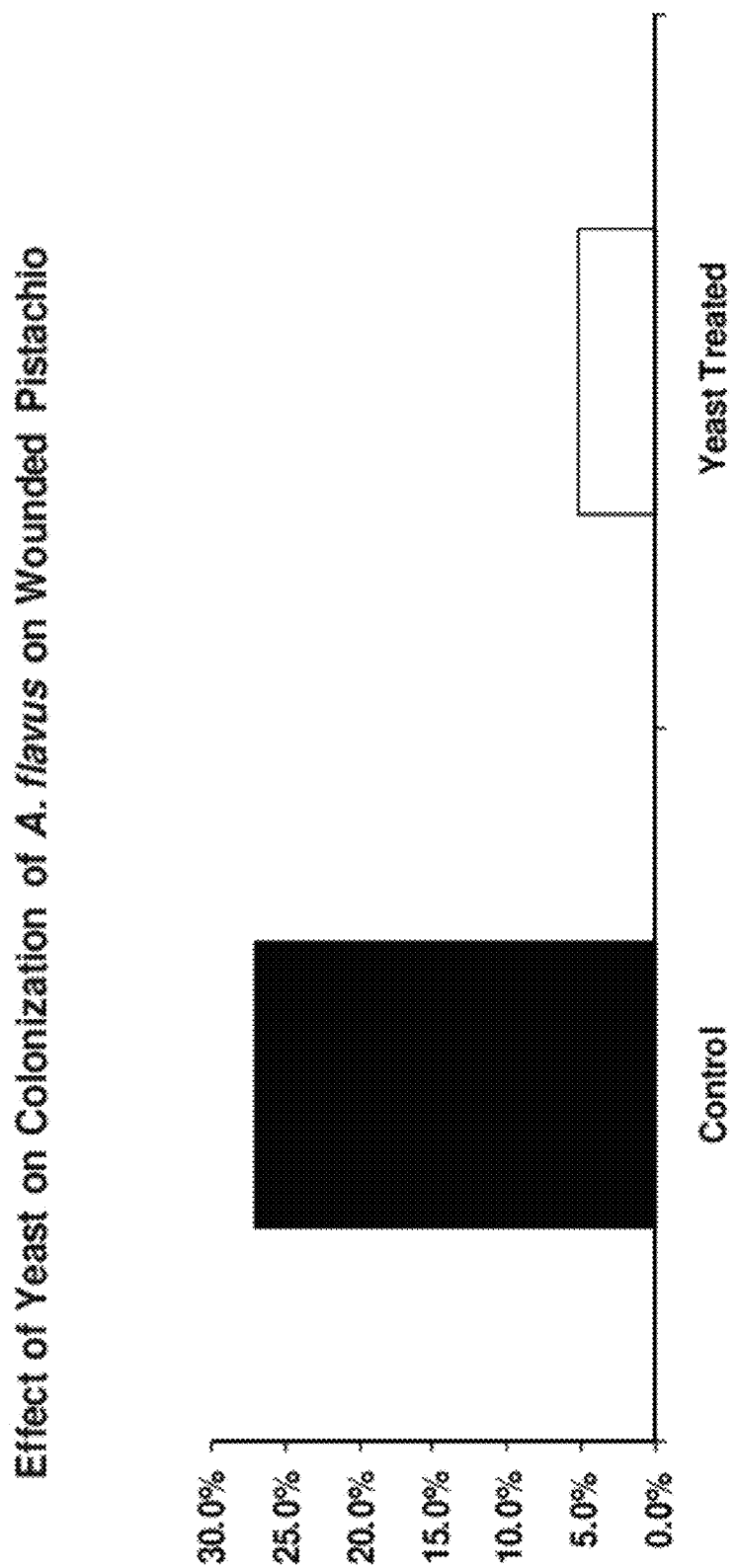
FIG. 5. is a graph of the effect of yeast on colonization of *Aspergillus flavus* on wounded pistachio nut-fruits.
Figure 6:
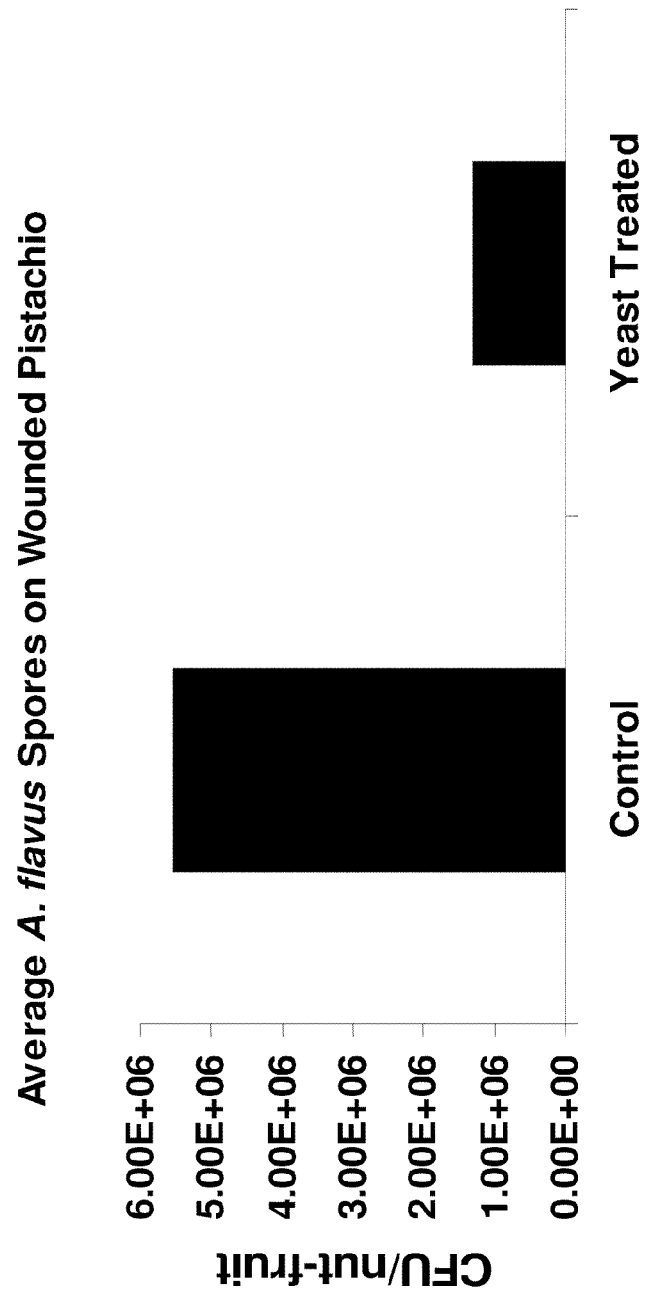
FIG. 6. is a graph of the reduction of *Aspergillus flavus* spores by yeast on wounded pistachio nut-fruits. Spores were enumerated by plating the samples on nutrient agar plates.

The yeast strain, *P. anomala* WRL-076 was maintained on potato-dextrose agar (PDA, Difco, Detroit, Mich.). Yeast suspension was prepared in sterile water. A Beckman-Coulter Multisizer was used to determine the number of yeast cells. Microorganisms were eluted in Tween 80 solution from the experimental samples by shaking and sonicating in flasks. A spiral plating system was used to spread the microorganisms onto nutrient agar. Viable counts of yeast were determined by spreading the yeast on dichloran rose bengal chloramphenicol (DRBC) agar plate. Pistachio nut-fruits on the tree were individually wounded with a dental needle and sprayed with aqueous suspension of yeasts at $3 \times 10^7$ cells/ml in August. The wounded nut-fruits without yeast-spray were used as controls. Five weeks after the yeast spray, wounded nut-fruit was hand picked from the tree and immediately placed to a special agar medium and incubated at 28° C. for eight days. The viable fungal and yeast counts on individual nut were enumerated by standard microbiological techniques. In order to see the variation among the nuts, every single nut collected was analysed for colonization of *A. flavus* and viable spores production. The percent colonization of *A. flavus* on nut-fruits was 27.1% for the control and 5.1% for the yeast treated nut-fruits (FIG. 5). The CFU of *A. flavus* spores from each single nut was enumerated. Average spore production in *A. flavus* infected nuts was $5.6 \times 10^6$ and $1.3 \times 10^6$ (FIG. 6). The total number of *A. flavus* spores produced on wounded pistachios in the control is $1.28 \times 10^8$ and for yeast sprayed pistachios is $5.2 \times 10^6$ respectively. A 96% reduction in spore number present in the orchard environment. The experiments demonstrated that the yeast, *P. anomala* can modulate spore production of *A. flavus* on wounded pistachio nut-fruits and is very powerful in reducing the spore production of *A. flavus*. This unique biocontrol activity of *P. anomala* WRL-076 can prevent further infection of *A. flavus* to pistachio nuts during the growing season in orchards.

Example 5

Control of *A. flavus* Isolated From Corn Kernels by *P. anomala* WRL-076

Figure 7:
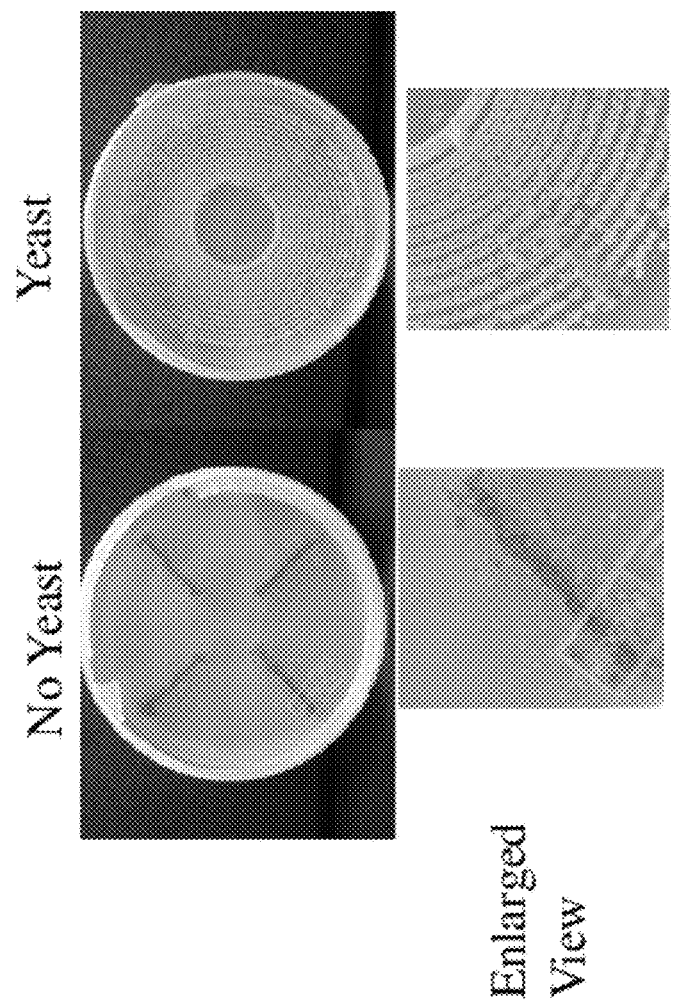
FIG. 7. is a photo of the biocontrol of *Aspergillus flavus* isolated from corn kernels by *Pichia anomala* WRL-076.

Thirty five strains of *A. flavus* were isolated from corn kernels. *P. anomala* WRL-076 shows good control of these strains by the two streak bioassay, on PDA. The efficacy of the biocontrol yeast, *P. anomala* WRL-076 has also been demonstrated by using Autoplate 4000 to spread the yeast at $10^6$ cells/ml in a controlled manner exponentially onto corn meal (made of grounded corn kernels) agar. 5 µl of *A. flavus* spores at $2 \times 10^5$/ml was pipeted onto each quarter of the agar plates in a thin line from the center towards edge of the plates (FIG. 7). The corn meal agar plate without yeast was used as the control. The inoculated plates were incubated at 28° C. for 7 days. Spore production on the agar plates were recorded by using a digital camera. The dense oliver green spores on corn meal agar can be easily visualized. In contrast the corn meal agar spread with the yeast showed very significantly less spores. The results indicate that the yeast has the potential to control *A. flavus* associated with corn.

Example 6

Control of *A. flavus* Under Water Stress

Figure 8:
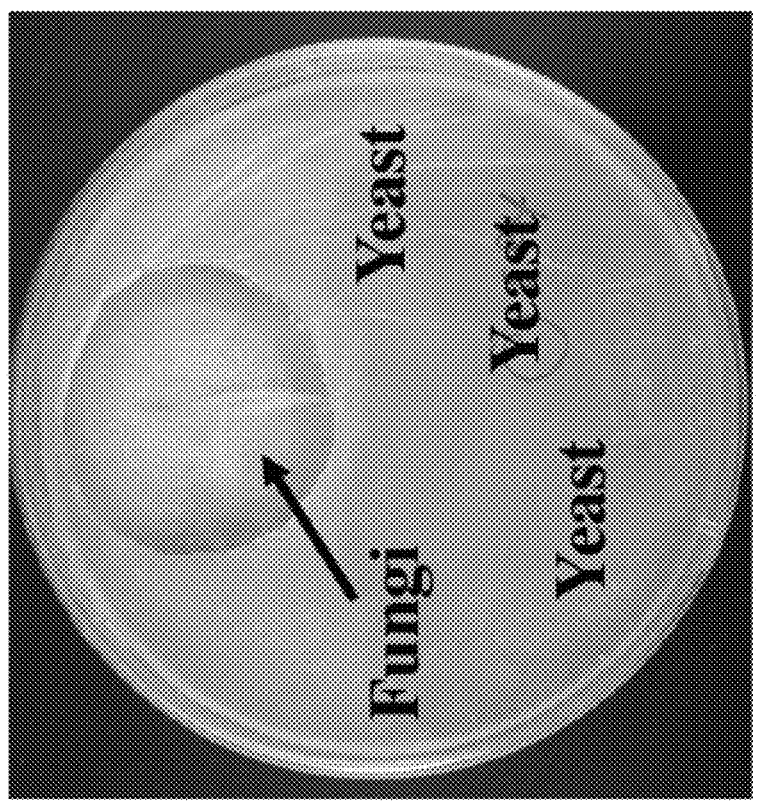
FIG. 8. is a photo of the biocontrol of *Aspergillus flavus* by *Pichia anomala* WRL-076 at low water activity. Polyethylene glycol 8000 was used to adjust the water in the medium.

In general, antagonists applied to crops for control of foliar diseases are exposed to environmental stresses such as temperature fluctuation and water availability. In laboratory experiments, PEG (polyethylene glycol) 8000 was used to adjust medium $a_w$ to 0.96, which mimicked a water stress condition of −5.62 MPa. *P. anomala* WRL-076 could grow at this low water activity ($a_w$). Spores of *Aspergillus flavus* were inoculated at one corner of PD broth containing PEG and incubated at 25° C. for three days, then the yeast cells were inoculated at the opposite corner and incubated for additional 7 days. The yeast cells formed a film and inhibited the growth of *A. flavus* inoculated to the medium (FIG. 8).

Example 7

Inhibition of a Wide Range of Pathogenic Fungi by *P. anomala* WRL076

In addition to *A. flavus* the yeast was shown to be antagonistic to several other filamentous fungi such as *Aspergillus ochraceus, Fusarium* spp., *Penicillium* spp, *Botrytis cinera, Alternaria* spp by using the bioassays developed for *A. flavus*. Some of these pathogenic fungi produce mycotoxins such as ochratoxin, fumonisin, patulin etc., which are harmful to animal and human health.

Example 8

Inhibition of Gram Negative Bacteria by *P. anomala* WRL-076

Figure 9:
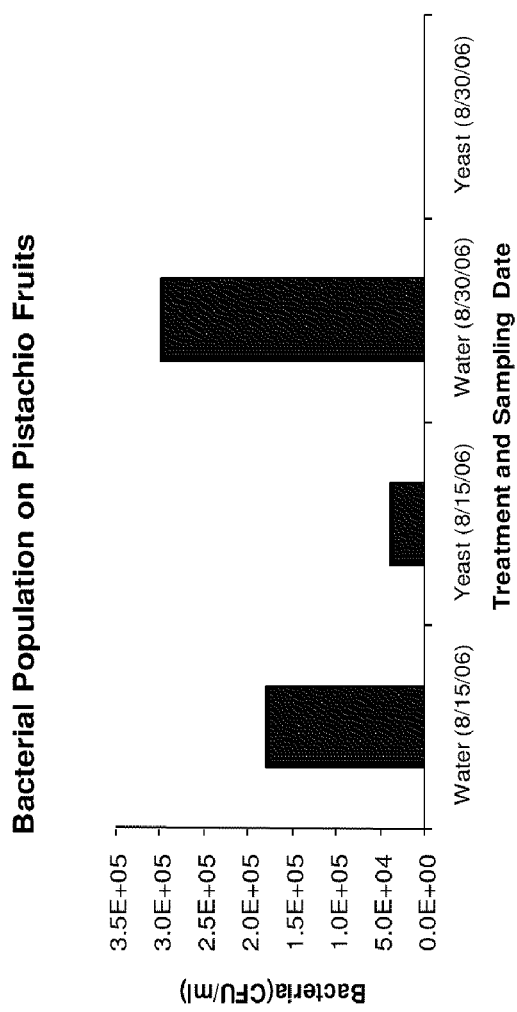
FIG. 9. is a graph of the effect of yeast on the population of *Burkholderia cepacia*. Yeast cells were sprayed to the pistachio trees. Nut-fruit samples were collected and enumerated for the number of bacteria.

Field experiments were conducted in a commercial pistachio orchard. Trees were sprayed with yeast cells which were suspended in water. Another group of trees were sprayed with water without any yeast and used as the control. For the water treatment, a dominant bacterium species appeared on the pistachio nut fruits and leaves. The bacterium was identified as the human pathogen, *Burkholderia cepacia*, by sequencing the 16 S ribosomal PCR fragment. The source of the bacterium was found in a local water supply. Leaves and nut-fruits from trees sprayed with yeast cells had a much reduced number of the bacterium. FIG. 9 shows the bacterial population on pistachio nut-fruits for yeast treated and water treated samples. The results demonstrated that the yeast inhibited the growth of the bacterium.

Example 9

Viability of Stored Yeast Cells

Figure 10:
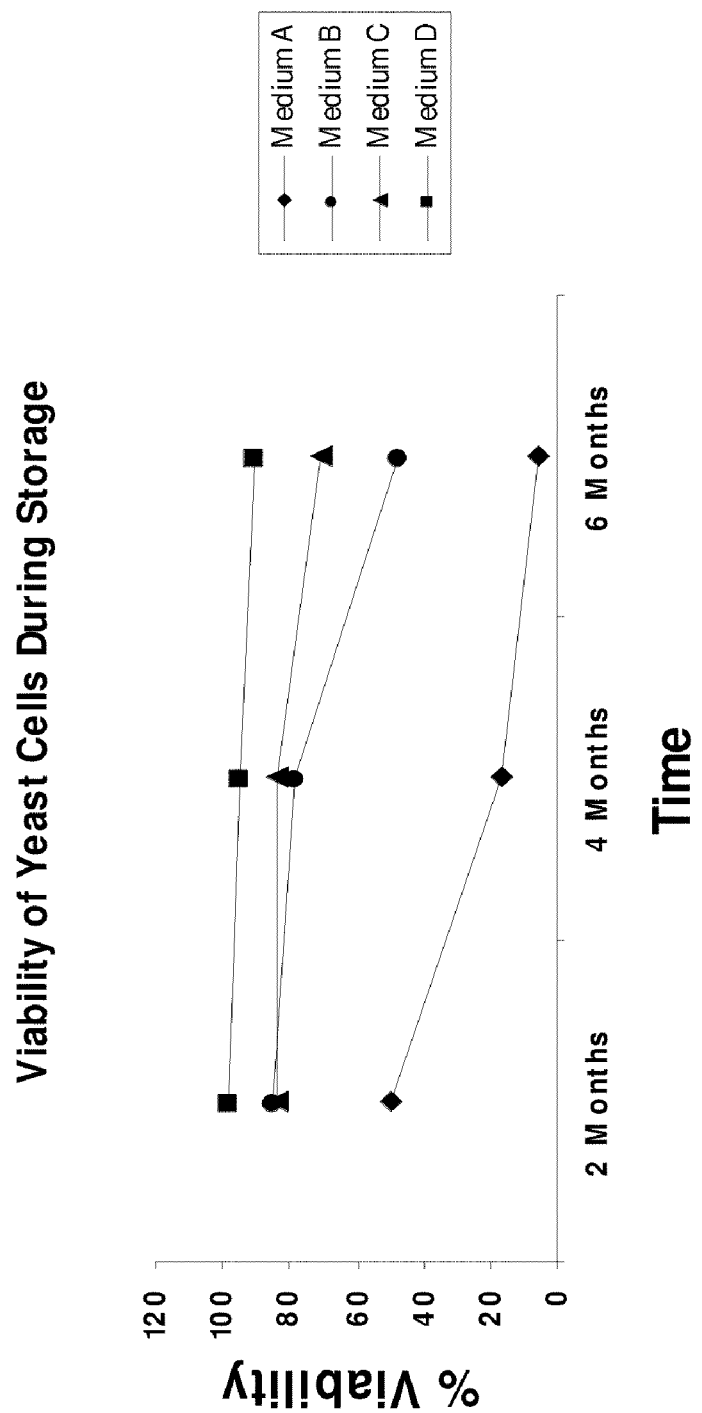
FIG. 10 is a graph of the viability of *Pichia anomala* during long term storage.

Yeast cells of *P. anomala* were maintained on potato dextrose agar (PDA). Yeast cells were remove from the agar plate and resuspended in a solution containing 0.9% sodium chloride and 0.01% Tween 80. The number of cells in the suspension were counted by a Hemocytometer. 100 ml of medium was dispensed to a 500 ml of Erlenmeyer flask. Yeast cells in the suspension were used to inoculate the medium. Sufficient yeast cells were added to the medium to achieve a concentration of $10^5$ cells/ml. The inoculated medium flask was transferred to an incubator equipped with a platform shaker. The yeast culture was grown for 72 hours at 28° C. and shaker was rotated at 150 RPM for aeration. The yeast cells were serially diluted and plated onto DRBC (Dichloran Rose Bengal Chloramphenicol) agar plate. *P. anomala* grew to a concentration of several billion yeast cells per milliliter in 72 hours. This amount of yeast cells can be diluted several hundred fold for most biocontrol spray application. Flasks containing the yeast cells were stored in a refrigerator for up to six month. The % viability of the yeast cultures from four different growth medium, A, B, C and D is summarized in FIG. 10.

Example 10

Intracelluar and Supernatant Sugar and Polyol Concentrations

Yeast cells in a 15 ml conical tube were harvested by centrifugation using a Sorvall RC-5C Plus centrifuge. The cell pellet was suspended in 1 ml dist. water. Yeast cells were disrupted in a Branson Sonifier® cell disrupter (Branson Ultrasonic Corp., Danbury, Conn.) for 2 min., then boiled for 5 min. and cooled down to room temperature. Acetonitrile was added to each tube to a final concentration of 75%. After votexing, the mixture in each tube was centrifuged in a Sorvall RC-5C Plus centrifuge for 10 min. The supernatant containing extracted sugars and polyols was filtered and transferred to a glass vial.

A high-performance liquid chromatographic method (HP ChemStation, Agilent Technologies, Santa Clara, Calif.) with evaporative light-scattering detection (PL-ELSD, Amherst, Mass.) was used for analysis of intracellular sugars and polyols. Separation of these compounds was achieved on a Prevail™ Carbohydrate ES HPLC column (Alltech Associates, Inc., Deerfield, Ill.). The mobile phase was acetonitrile:water 75:25 (v/v), at a flow rate of 1 ml/min.

Figure 11:
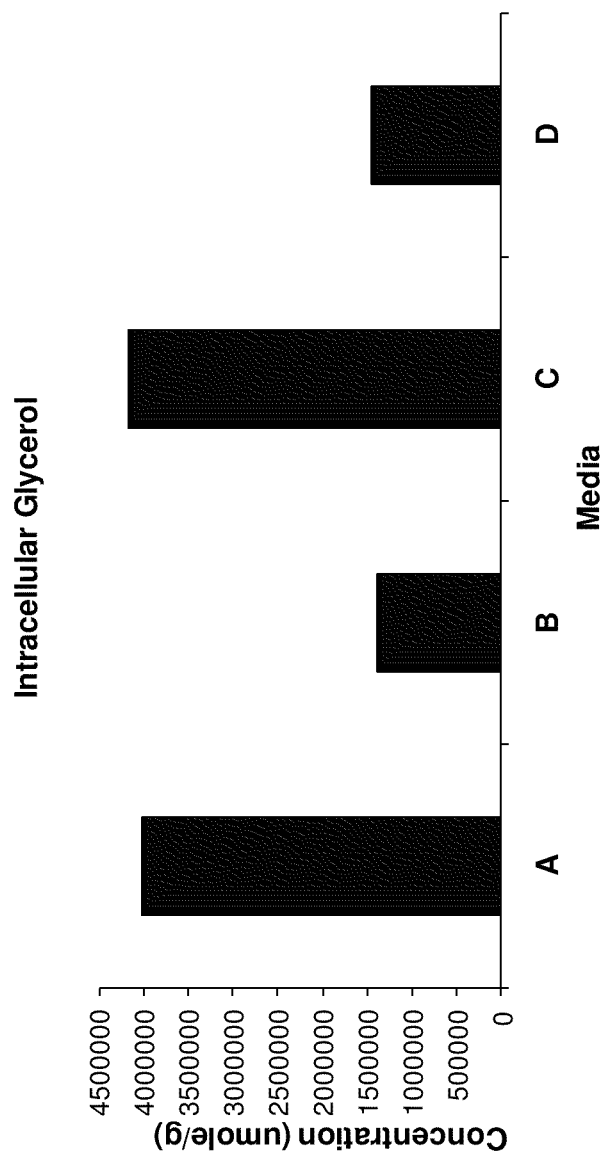
FIG. 11 is a graph of intracellular glycerol concentrations in cells of *Pichia anomala*.
Figure 12:
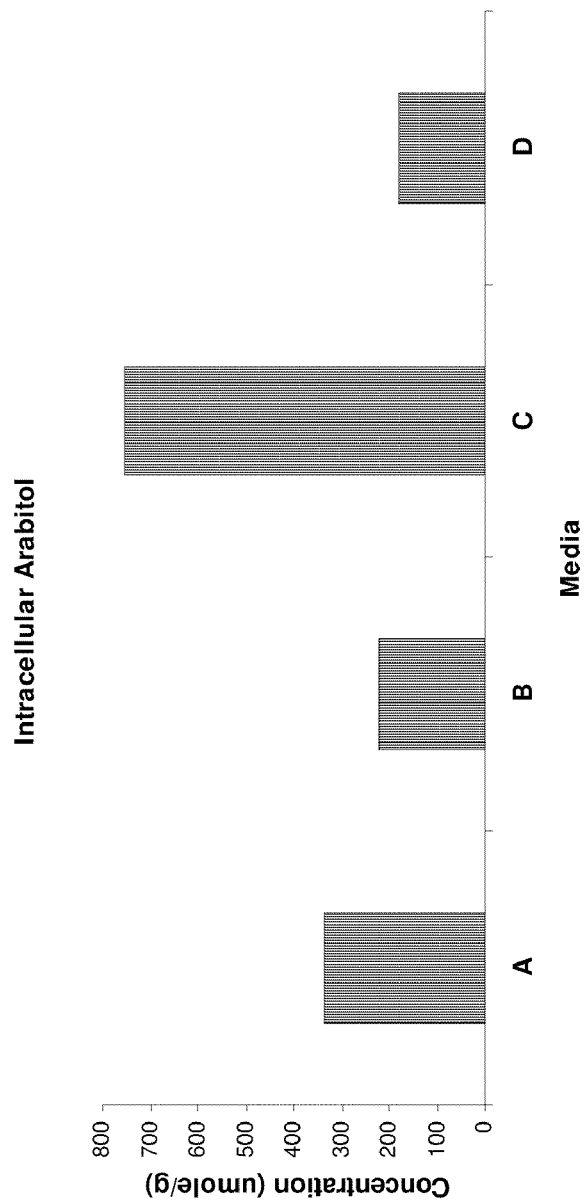
FIG. 12 is a graph of intracellular arabitol concentrations in cells of *Pichia anomala*.
Figure 13:
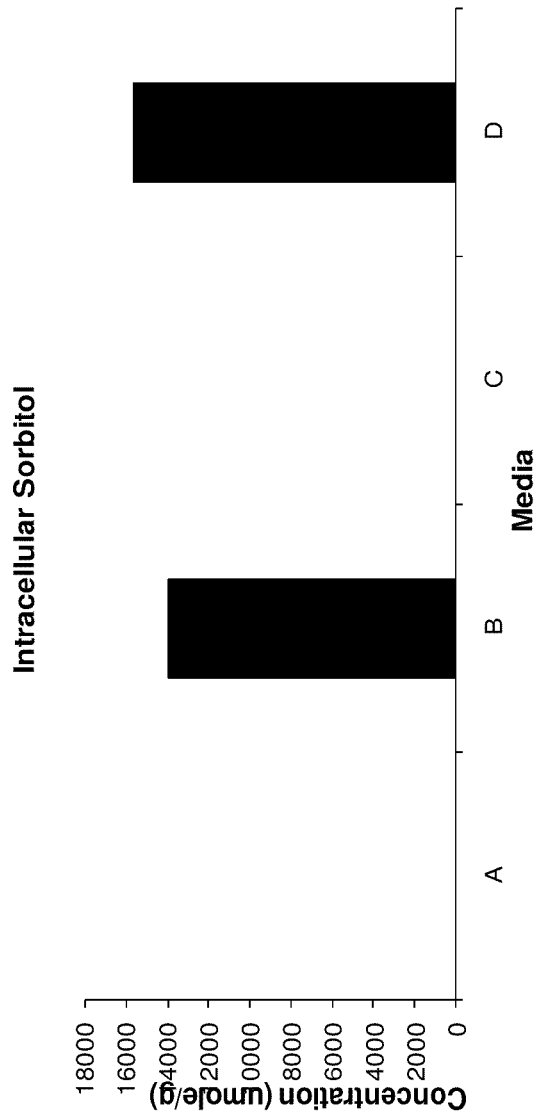
FIG. 13 is a graph of intracellular sorbitol concentrations in cells of *Pichia anomala*.
Figure 14:
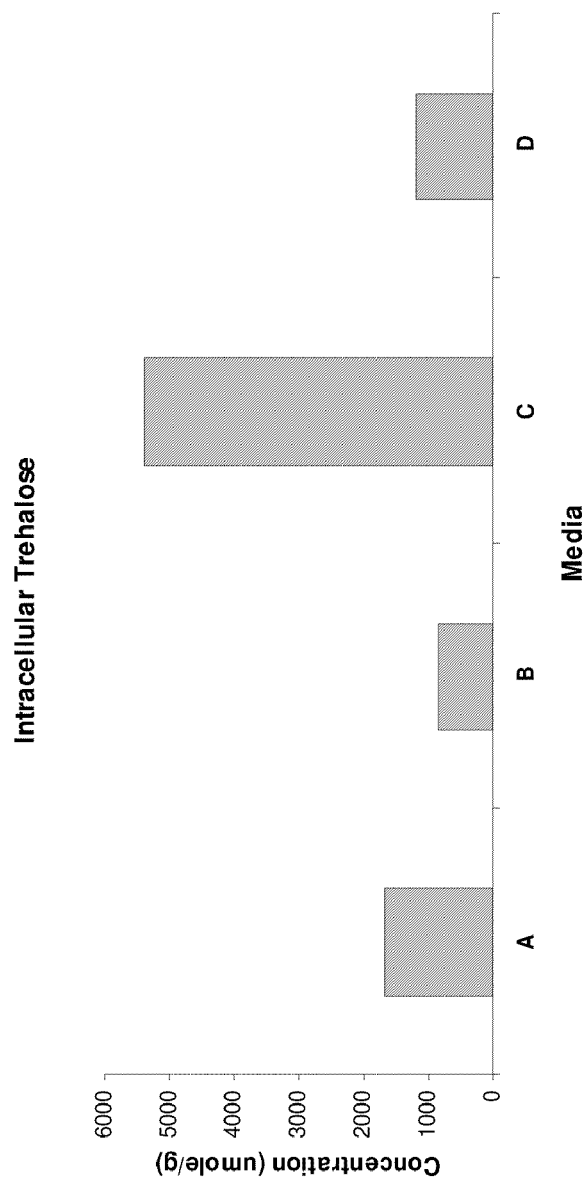
FIG. 14 is a graph of intracellular trehalose concentrations in cells of *Pichia anomala*.
Figure 15:
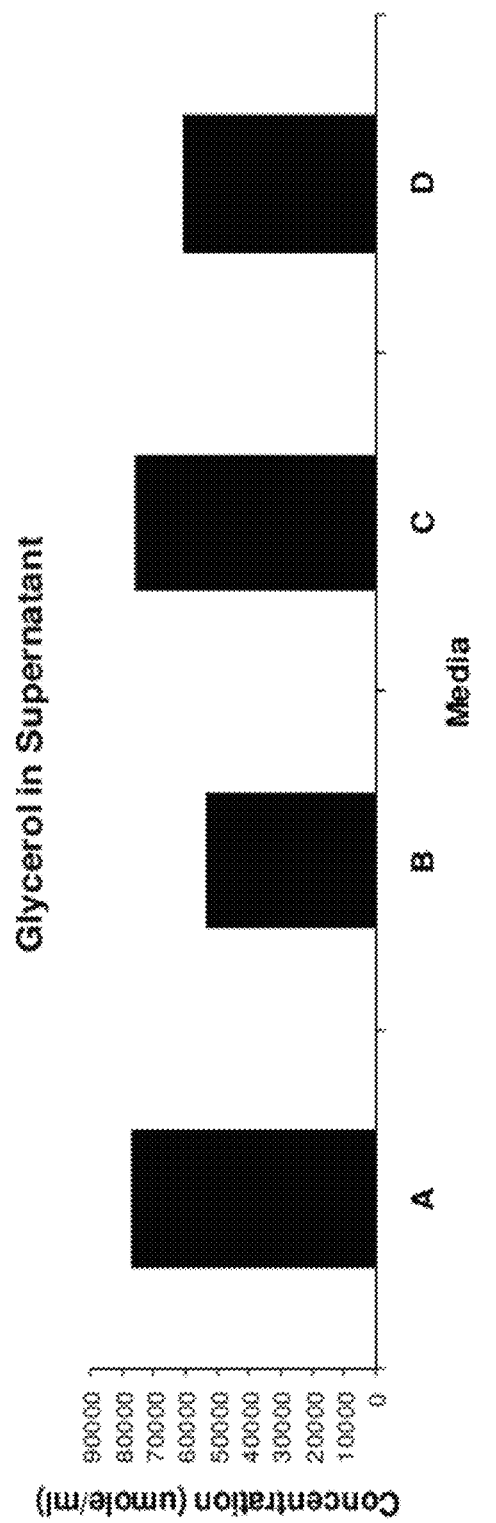
FIG. 15 is a graph of glycerol concentrations in the supernatant of *Pichia anomala*.
Figure 16:
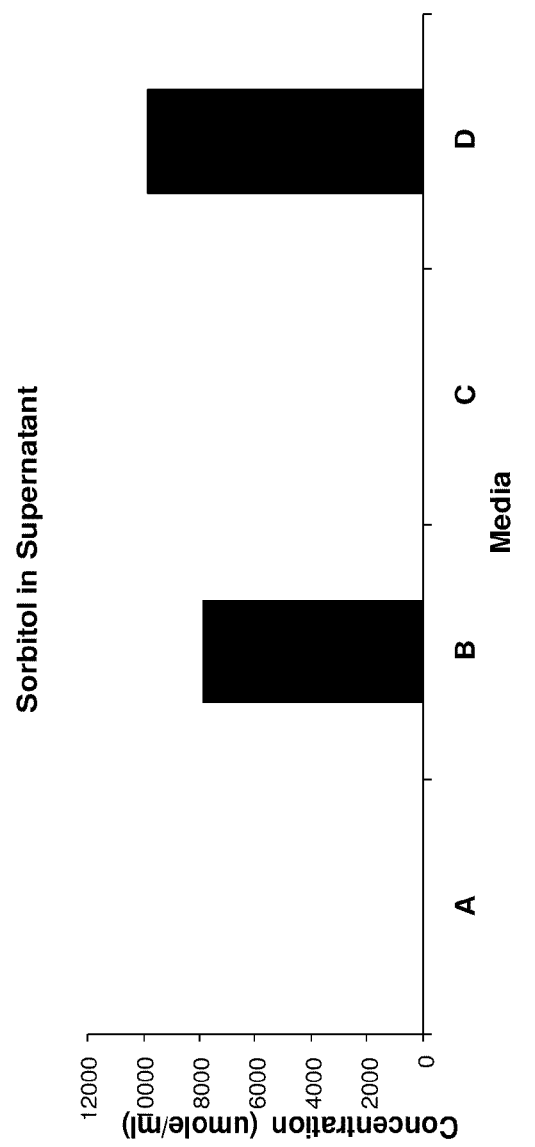
FIG. 16 is a graph of sorbitol concentrations in the supernatant of *Pichia anomala*.

Intracellular glycerol was found to accumulate in yeast cells grown in the medium A, B, C and D but the concentrations were not the same. In medium B and D, sorbitol was used as one of the carbon source, intracellular glycerol was 3 fold lower (FIG. 11). Arabitol accumulated inside the yeast cells grown in all the four media. The concentrations were much lower comparing to glycerol (FIG. 12). Intracelluar sorbitol was only found in yeast cells grown in media containing sorbitol as one of the carbon sources, i. e. medium B and D. Trehalose was accumulated in yeast cells grown in all four medim. Sorbitol in the medim B and D apparently suppressed the accumulation of trehalose. The results of the analysis are presented in FIGS. 11, 12 and 14. Glycerol was found to be exported out to the growth medium by *Pichia anomala*. Sorbitol was found to be in the supernatants for cells grown in medium B and D (FIG. 16).

Figure 17:
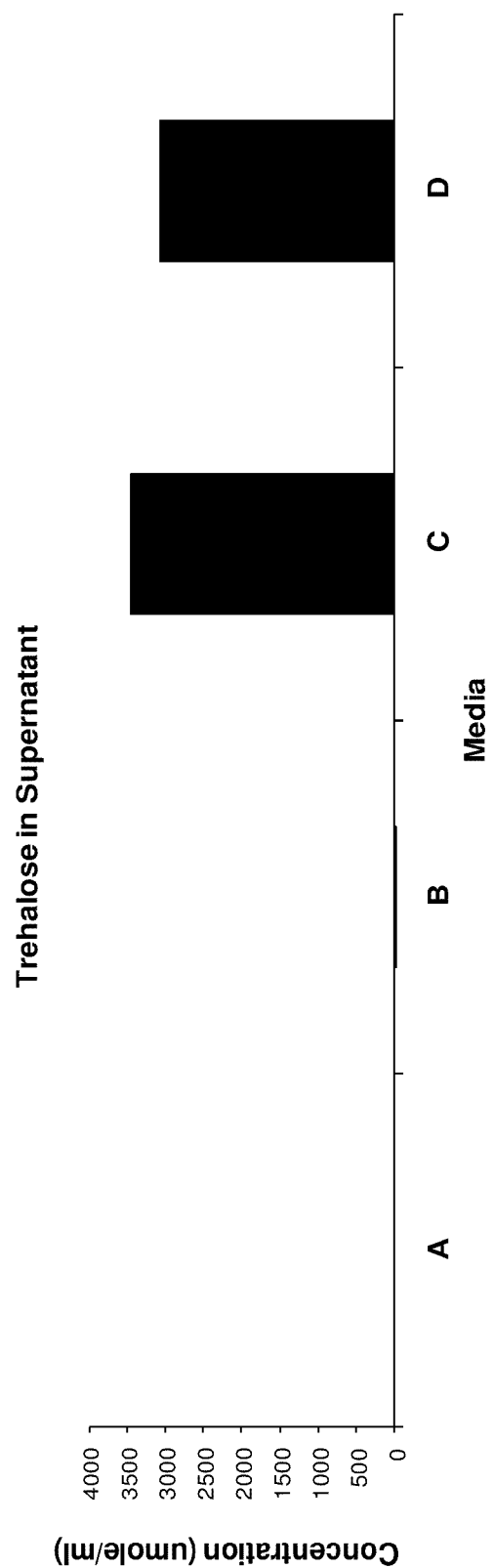
FIG. 17 is a graph of trehalose concentrations in the supernatant of *Pichia anomala*.

Trehalose was found to be in the supernant when cells grown in medium C and D (FIG. 17). *Pichia anomala* cells grown in medium D had intracellular glycerol, arabito, sorbitol and trehalose accumulation as well as I fairly amount of glycerol, sorbitol and trehalose in the supernatant. The polyol and trehalose may have a synergistic effect on prolonging the viability of yeast cells see FIGS. 10 and 11).

Example 11

Reduction of *Asperaillus flavus* Population in Pistachio Orchard

Experimental Design

Two experiments were conducted in a commercial orchard. Nut-fruits of pistachio were individually wounded with a dissecting needle. Four treatments were applied: W-sprayed with water; Y-sprayed with an aqueous suspension of yeasts at $5 \times 10^7$ cells/ml; Y+AF-sprayed with an aqueous suspension of yeasts at $5 \times 10^7$ cells/ml and two hours later sprayed with spore suspension of *A. flavus* at $1 \times 10^3$ cells/ml; AF-sprayed with spore suspension of *A. flavus* at $1 \times 10^3$ cells/ml. The wounded nut-fruits were harvested on Aug. 11, 2005 and Aug. 31, 2005 respectively for Exp. 1 (Jun. 30 to Aug. 11, 2005) and Exp. 2 (Aug. 11 to 30, 2005).

Sample Collection

Wounded pistachio nut-fruits were hand picked from the tree and immediately placed to test tubes (five nuts per tube). The samples were brought back to the lab for analysis. Six hundred nut-fruits from each treatment were analysed in both experiment 1 and 2 to provide sufficient replications for statistical analysis.

Colony Forming Unit

Microorganisms kept in the tubes were eluted from nut-fruits in Tween 80 solution from the experimental samples by shaking and sonicating. Viable counts of yeast cells and *A. flavus* propagules were determined by spreading the microorganisms on dichloran rose bengal chloramphenicol (DRBC) agar plate using a spiral plating system (Spiral Biotech Autoplate 4000).

Figure 18:
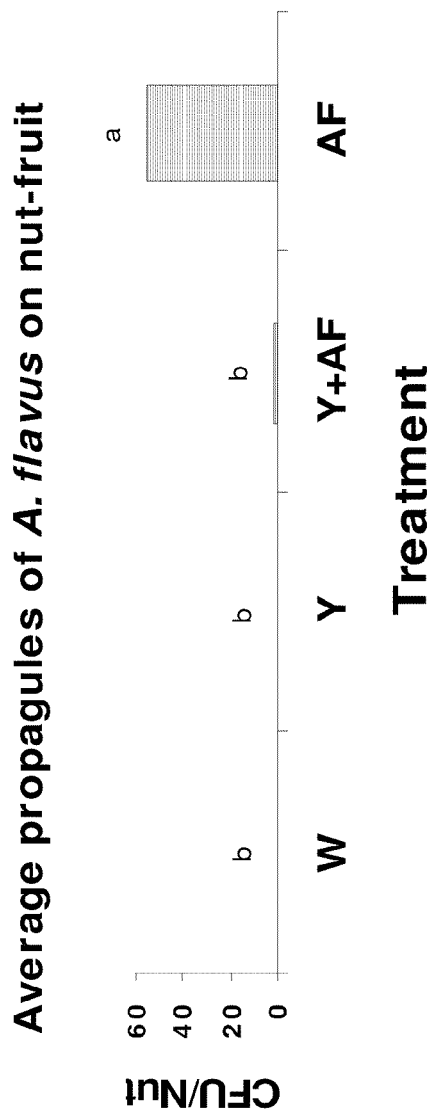
FIG. 18 is a graph of the growth inhibition of *Aspergillus flavus* by *Pichia anomala*.
Figure 19:
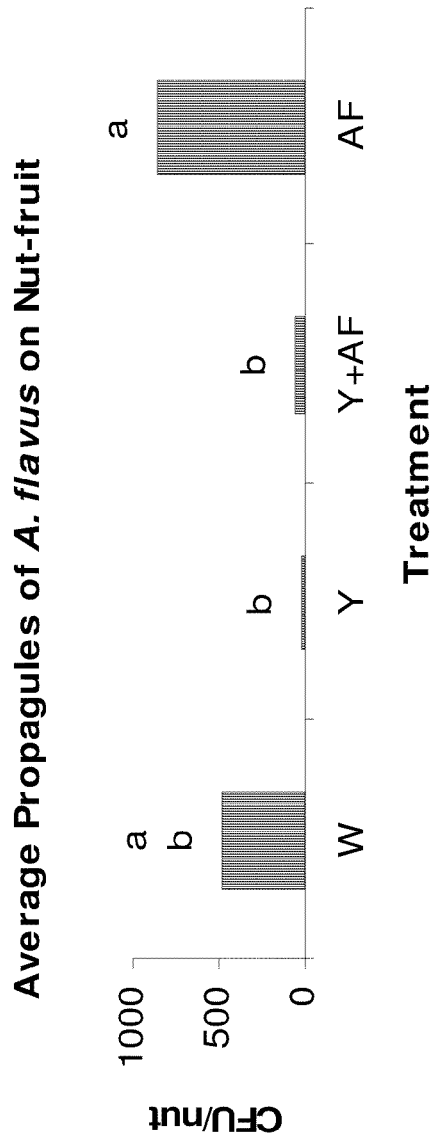
FIG. 19 is a graph of the growth inhibition of *Aspergillus flavus* by *Pichia anomala*.

The propagules of *A. flavus* from harvested samples were extracted and spreaded on DRBC plates to determine the CFU (colony forming unit). FIG. 18 shows the data for the total number of propagules in the four treatments of Exp. 1. The results indicate that the CFUs of *A. flavus* in nut-fruits sprayed with AF are 40 times more than the nut-fruits treated with Y+AF. It equivalents to 98% reduction of *A. flavus* population in the orchards. Similar results are observed in the second experiment (Exp 2). By comparing water sprayed nut-fruits to yeast sprayed ones, *A. flavus* population was reduced 97% by the yeast treatment. As shown in FIG. 19, a 75% reduction of *A. flavus* is accounted due to the spray of *P. anomala*.

Example 12

Efficacy of *Pichia anomala* WLR-076 to Control Aflatoxin on Corn in Texas

Figure 20:
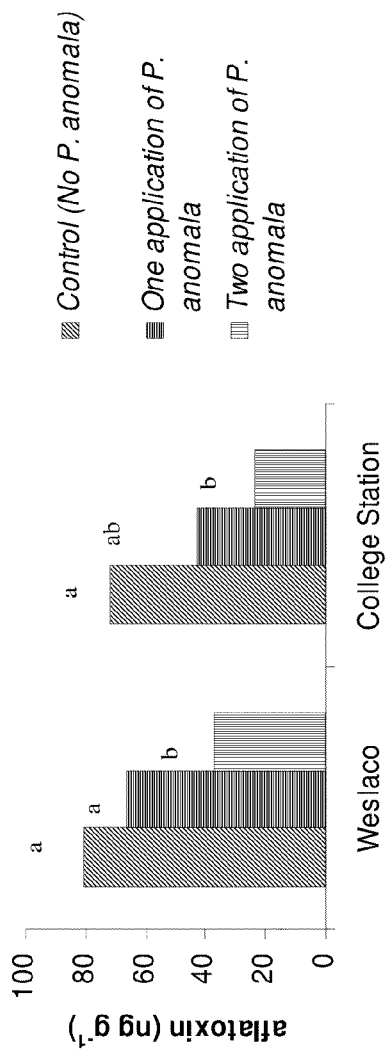
FIG. 20 is a graph of the efficiency of *Pichia anomala* to reduce aflotoxin in corn.

The experiments were conducted by Tom Isakeit at three Texas Agricultural Experiment Stations: Weslaco (WE) and College Station (Burleson County) (CS). The yellow corn hybrid 'Pioneer Brand 31B13' was planted 17 March in WE on a Harlingen clay and 5 April in CC on a Victoria clay. Each replicate consisted of four, 7.3 m rows, with a 76 cm row spacing and 30 cm plant spacing. There were five replicates per treatment (six in CC) arranged in a randomized complete block design. The treatments were: (1) *P. anomala* WLR-076 applied when corn was at 50% silking; (2) *P. anomala* WLR-076 applied when corn was at 50% silking, then again two days later; (3) no yeast application (control). Only the top ears of corn in the two middle rows of replicates were treated. All plots were inoculated with *Aspergillus flavus* by placing corn kernels colonized by the fungus on the ground in between the rows (1 kg dry weight basis per 61 m), two days after the first application of *P. anomala*. *A. flavus* inoculum was prepared as follows: commercial deer corn was soaked overnight in water, the water was drained and 5.6 kg (dry weight basis) aliquots of corn in polypropylene trays were autoclaved 90 min. After the corn had cooled, aliquots were placed in translucent polyethylene bags and inoculated with $2 \times 10^{10}$ conidia of *A. flavus* NRRL 3357 in 500 ml water. The bags, left slightly open, were placed under a greenhouse bench and incubated at ambient temperature (27° to 32° C.) for 3-4 days. *P. anomala* was prepared from a paste concentrate by diluting it in 8 L water to a concentration of $1.6 \times 10^7$ to $3.2 \times 10^7$ colony-forming unit/ml. The yeast suspension was sprayed onto silks and adjacent portions of ears until run-off using a backpack sprayer and a hollow cone nozzle. The top ears from the two middle rows of plots were harvested 13 July, 8 August, and 17 August, in WE, CC and CS, respectively. Ears were husked, dried, shelled and bulked. The sample size was 4.2 to 8.6 kg per replicate, originating from 40 to 60 ears. All corn from each replicate was ground using a Romer mill (Romer Labs, Union, Mo.) and aflatoxin was quantified from 50-g subsamples using the VICAM Aflatest fluorometer USDA-FGIS procedure (VICAM, Watertown, Mass.). The results are summarized in FIG. 20.

What is claimed is:

1. A method for growth of a biologically pure culture of a yeast having all of the identifying characteristics of the deposited sample identified as WRL-076 (NRRL Y-30842), comprising inoculation of the yeast in a growth media containing trehalose, glucose and sorbitol.

2. The method of claim 1, wherein the trehalose is at a concentration range of about 1% to about 5% (w/v).

3. The method of claim 1, wherein the sorbitol is at a concentration range of about 1% to about 5% (w/v).

4. A method for combating deleterious microorganisms in flowering agricultural crops comprising, placing a dispenser containing as an active ingredient, a biologically effective amount of biologically pure yeast *Pichia anomala* having all of the identifying characteristics of the deposited sample identified as WRL-076 (NRRL Y-30842), in a bee hive.

\* \* \* \* \*

SEQUENCE LISTING

```
<160> NUMBER OF SEQ ID NOS: 1

<210> SEQ ID NO 1
<211> LENGTH: 574
<212> TYPE: DNA
<213> ORGANISM: Pichia anomala WRL-076
<300> PUBLICATION INFORMATION:
<308> DATABASE ACCESSION NUMBER: NRRL/Y-30842
<309> DATABASE ENTRY DATE: 2005-05-09
<313> RELEVANT RESIDUES IN SEQ ID NO: (1)..(574)
```

```
<400> SEQUENCE: 1
ccacagggat tgcctcagta cggcgactga agcggcaaaa gctcaaattt gaaatctagc      60
accttcggtg ttcgagttgt aatttgaaga tggtaacctt gggtttggct cttgtctatg     120
ttccttggaa caggacgtca tagagggtga gaatcccgtc tgatgagatg cccattccta     180
tgtaaggtgc tatcgaagag tcgagttgtt tgggaatgca gctctaagtg ggtggtaaat     240
tccatctaaa gctaaatatt ggcgagagac cgatagcgaa caagtacagt gatggaaaga     300
tgaaaagaac tttgaaaaga gagtgaaaaa gtacgtgaaa ttgttgaaag ggaagggcat     360
tagatcagac ttggtgtttt acgattatct tctcttcttg agttgtgcac tcgtatttca     420
ctgggccagc atcgattcgg atggcaagat aatggcagtt gaatgtggct tcacttcggt     480
ggagtgttat agcttctgct gatattgcct gtctggatcg agggctgcgt cttttgacta     540
ggatgctggc gtaatgatct aatgccgccc gtcg                                 574
```